United States Patent [19]
Ryu et al.

[11] Patent Number: 5,811,623
[45] Date of Patent: Sep. 22, 1998

[54] ISOMERIZATION OF OLEFINS BY ALKYLATION AND DEALKYLATION OF AROMATIC HYDROCARBONS

[75] Inventors: J. Yong Ryu; Willibrord A. Groten, both of Pasadena, Tex.

[73] Assignee: Catalytic Distillation Technologies, Pasadena, Tex.

[21] Appl. No.: 872,003

[22] Filed: Jun. 9, 1997

[51] Int. Cl.$^6$ .................................................... C07C 5/27
[52] U.S. Cl. .......................... 585/671; 585/316; 585/324
[58] Field of Search ..................... 585/316, 324, 585/466, 467, 483, 671; 203/DIG. 6

[56] References Cited

U.S. PATENT DOCUMENTS

| | | | |
|---|---|---|---|
| 3,121,124 | 2/1964 | Verdol | 260/677 |
| 4,045,506 | 8/1977 | Simic et al. | 260/677 A |
| 4,499,321 | 2/1985 | Sato et al. | 585/486 |
| 4,691,073 | 9/1987 | Michaelson | 585/639 |
| 4,714,788 | 12/1987 | Michaelson et al. | 568/697 |
| 4,849,569 | 7/1989 | Smith, Jr. | 585/446 |
| 4,891,458 | 1/1990 | Innes et al. | 585/323 |
| 4,935,577 | 6/1990 | Huss, Jr. et al. | 585/726 |
| 5,057,635 | 10/1991 | Gajda | 585/259 |
| 5,059,741 | 10/1991 | Foley | 585/734 |
| 5,132,484 | 7/1992 | Gajda | 585/667 |
| 5,243,116 | 9/1993 | Lee et al. | 585/467 |
| 5,365,008 | 11/1994 | Barger et al. | 585/667 |

FOREIGN PATENT DOCUMENTS

| | | | |
|---|---|---|---|
| 0390596 | 3/1990 | European Pat. Off. | C07C 22/66 |
| 0501577 | 2/1992 | European Pat. Off. | C07C 5/27 |
| 0523838 | 6/1992 | European Pat. Off. | C07C 5/23 |
| WO9323353 | 11/1993 | WIPO | C07C 5/27 |
| WO9533704 | 12/1995 | WIPO | C07C 41/09 |

OTHER PUBLICATIONS

*Pure Isobutylene from $C_4$ Mix*, Hydrocarbon Processing, Aug., 1987—Marcelino Miranda.
*The Reaction of p–Substituted t–Butylbenzene over Silica–Alumina Catalyst*; Kinetics & Catalysis (IV) pp. 291–296 Takeshige Takahashi & Michiaki Nomura.
*On the Mechanism of Contact Eliminations XXX. The Cracking of Butyl–Benzenes Over Silica–Alumina Catalysts*, Journal of Catalysis 21, 255–262 (1971); P. Andreu, G. Martin and H. Noller.
*Acidic and Cataytic Properties of Aluminesilicate Cracking of Isooctane and tert–Butylbenzene* pp. 318–321; A. Beglaryan and B. V. Romanovskii Chemistry Faculty, M. V. Lomonosov Moscow State University.
*Reversible Dealkylation of Protonated tert–Butylbenzene Position of the Equilibrium*, Dan Farcasiu, 1979 American Chemical Society, J. Org. Chem. vol. 44, No. 13, 1979 pp. 2103–2105.
*Alkylbenzenes. V. Introconversion of sec–Butylbenzene and Isobutylbenzene*, Dept. of Chem. Univ. of Texas pp. 640–643, vol. 81, R. Roberts, Yuri Han, Calvin Schmid & Donald Davis.

*Primary Examiner*—Glenn Caldarola
*Assistant Examiner*—Thuan D. Dang
*Attorney, Agent, or Firm*—Kenneth H. Johnson

[57] ABSTRACT

A isomerization process for $C_4$ to $C_{15}$ olefins carried out by the reaction of $C_4$ to $C_{15}$ olefins, having a first skeletal distribution, with aromatic compounds under alkylation conditions to produce an alkylated aromatic product, dealkylation of the alkylated aromatic product under dealkylation conditions to produce a dealkylated product comprising said aromatic compounds and olefins corresponding to the olefins in the alkylation and having a second skeletal distribution different than said first skeletal distribution. Acidic catalysts such as molecular sieves are used in both alkylation and dealkylation. The reactions may be carried out in either straight pass fixed beds or in catalytic distillation reactors.

32 Claims, 3 Drawing Sheets

ISOMERIZATION OF OLEFINS BY ALKYLATION AND DEALKYLATION OF AROMATIC HYDROCARBONS

BACKGROUND OF THE INVENTION

1. Field of The Invention

The present invention relates to a process for the skeletal isomerization of olefins. More particularly the process involves aromatic alkylation/dealkylation to convert linear olefins to branched olefins (also referred to herein as isoolefins or tertiary olefins) and to separate olefins from paraffins.

2. Related Art

The skeletal isomerization of olefins is an important reaction for the fuel and chemical industries. For example, isomerization of n-butene to isobutylene and n-pentenes to isoamylenes has been practiced to produce isoolefins. Since n-pentenes have lower octane numbers than isopentenes, the n-pentene isomerization is useful for motor fuel production. The isomerization of n-butenes and n-pentenes to isoolefins used to produce oxygenates such as methyl tertiary butyl ether (MTBE) and tert-amyl methyl ether (TAME) is increasingly important for the formulation of reformulated gasoline (RFG). The ethers are used as octane improvers in gasoline and to reduce undesirable emissions.

Currently there is no simple technology to separate olefins from paraffins and convert linear olefins to branched olefins. Heretofore high purity isoolefins (primarily tertiary olefins) were primarily produced by separating tertiary olefins from the mixture of olefins using the "cold acid" process, i.e. sulfuric acid extraction, however sulfuric acid in general processes are not generally environmentally desirable nor is this process particularly cost efficient.

U.S. Pat. No. 3,121,124 (Shell) disclosed the removal of tertiary olefins from mixed streams by etherification and decomposition of the ether to recover the tertiary olefin in substantially pure form. Subsequently, other processes employing decomposition of ethers were disclosed in U.S. Pat. Nos. 4,447,668 (CR&L); 4,551,567 (CR&L); and 4,691,073 (Exxon). However, in these processes the linear olefins are substantially unaffected and the main result is to separate isoolefins from paraffins and linear olefins. The recovery of linear olefins as isoolefins is limited since they are usually present in too dilute a quantity for which there is no technology available to economically convert them to isoolefins.

Conventional fixed bed straight pass isomerizations of olefins are equilibrium limited, thus limiting practically achievable yield of isoolefins. The isomerizations are carried out using acidic catalysts such as molecular sieves and the like.

Skeletal isomerization has been carried out with acidic catalysts such as fluorinated alumina, SAPO (silicoaluminophosphates), ALPO (aluminophosphates), ferrierite, aluminosilicates, zeolites, clays, etc. It has been known that ferrierite and ZSM-35 are shape selective zeolite catalysts for n-butene skeletal isomerization to isobutylene. The most preferred mode of carrying out the isomerization is the vapor phase fixed bed operation, in which a tubular reactor is packed with heterogeneous acidic catalysts and the vapors of the olefinic hydrocarbon feed stocks are passed through the catalyst bed at the temperatures which are effective for the skeletal isomerization. Usually the double bond isomerization of olefins is much easier than the skeletal isomerization and hence the temperatures required for the double bond isomerization are much lower than the skeletal isomerization temperatures.

The skeletal alteration of alkyl groups of alkyl aromatic compounds such as butyl group of butylbenzene is another kind of isomerization which is different from olefin isomerization. R. M. Roberts et al (JACS Vol 81, 640, 1959) explained the structural isomerization between sec-butyl and isobutyl groups without breaking the butyl group from the benzene ring. The interconversion among sec-butylbenzene, isobutylbenzene and tert-butylbenzene is demonstrated by acid catalyzed reaction. The composition of the equilibrium mixture contains only a small amount of tert-butylbenzene, probably due to high instability of the tert-butylbenzene carbonium ion. The isomerization of butyl groups proceeds throughout the formation of a couple of intermediates, a σ-bonded complex intermediate first formed by the interaction of alkylaromatic compounds with an acidic site on a catalyst and then converted to a methyl-bridged π-complex intermediate.

The catalyst used in the conventional process for skeletal isomerization of olefins generally suffers relatively fast catalyst deactivation caused by deposition of heavy carbonaceous materials (coke) on the catalyst surface and pores. Therefore, there is always fast initial catalyst deactivation regardless of catalysts. Because of this fast initial catalyst deactivation and other competing reactions, the skeletal isomerization becomes impractical at the temperatures below about 350° C. Since the olefinic hydrocarbon feed stocks usually contain a small amount of dienes and alkynes in addition to olefins, the catalyst deactivation becomes even faster. Therefore, frequent catalyst regeneration is necessary. To overcome slower isomerization reaction rates, the reaction temperature has to be raised. This can lead to even faster catalyst deactivation and often increases the cracking reactions, producing lighter products than intended. Therefore, the catalyst regeneration or the replacement of deactivated catalyst with a fresh catalyst becomes necessary. In fact, often the catalyst regeneration cycle length is one of the major determining factors whether a process becomes commercially successful or not. Aromatic alkylation with olefins is widely practiced to produce various alkylated products and can be achieved with various acidic catalysts. Zeolite catalysts are known to be among the best for this purpose, see for example, U.S. Pat. Nos. 4,169,111 (Unocal); 4,301,310 (Mobile); 4,798,816 (Unocal); and 4,876,408 (Unocal); 4,891,458 (Chevron); 4,849,569 (CR&L); and 5,446,223 (CR&L).

Dealkylation is well documented. T. Takahashi et al (Kinetics & Catalysis (IV) 291) carried out vapor phase dealkylation of tert butyl aromatic compounds such as tert-butylbenzene, p-tertiary butyltoluene and p-tert butyl ethylbenzene over a silica-alumina catalyst. Tertbutyltoluene was dealkylated over a Y-zeolite catalyst. The dealkylation reactivities of three butylbenzene isomers over silica-alumina catalysts were investigated by P. Andreu et al (J of Catalysis, Vol. 21, 225, 1971). The reactivity decreases in order of tert-, sec- and n-butylbenzene. The dealkylation of tert-butylbenzene at 180° to 360° C. produced only isobutylene as olefin product.

Two different mechanisms are proposed for the dealkylation of sec-butylbenzene; one for the temperatures lower than 400° C. and the other for the temperatures higher than 400° C. The olefin products of dealkylation at temperatures below 400° C. contain little isobutylene. D. Farcasiu (J Org. Chem., Vol 44, No 13, 1979) investigated the acid catalyzed dealkylation of alkylbenzene compounds such as toluene, ethylbenzene, isopropylbenzene and tert-butylbenzene. The dealkylation of alkylaromatic compounds is suggested to occur through the sequential formation of two intermediates.

The first intermediate (charge delocalized phenyl cation) is formed by protonation of the benzene ring of alkylaromatic compounds. This intermediate decomposes to benzene, and the alkyl carbonium ion (the second intermediate). This second intermediate decomposes to olefin product with or without the skeletal isomerization. The first intermediate is identical to the intermediate proposed by R. M. Roberts for the interconversion of butyl groups of sec-butylbenzene and isobutylbenzene. Therefore, the works of R. M. Roberts and D. Farcasiu, referenced above, may explain the reaction mechanisms involved in the conversion of linear olefins to iso-olefins via the consecutive alkylation-dealkylation reactions disclosed in this invention.

U.S. Pat. No. 4,499,321 disclosed a selective dealkylation process of 1,4-dialkylbenzene from mixtures of dialkyl benzene by employing molecular sieve catalysts. This process is useful to prepare m- and p-cresols. A m- and p-cresol mixture is alkylated with isobutylene into a mixture of tert-butyl cresol isomers which are separated by distillation. The separated isomers are dealkylated to produce m- and p-cresols.

M. Miranda in Hydrocarbon Processing, pages 51–52, August 1987 describes a process for the recovery of pure isobutylene from $C_4$ mixtures by selective alkylation of phenol with isobutylene and dealkylation to recover the isobutylene.

Many of the types of processes described above are disclosed to be suitable for catalytic distillation reactions. In catalytic distillation or reactive distillation the components of the reaction system are concurrently separable by distillation, using the catalyst structures as the distillation structures. Such systems are described variously in U.S. Pat. Nos. 4,215,011 (CR&L); 4,232,177 (CR&L); 4,242,530 (CR&L); 4,250,052 (CR&L); 4,302,356 (CR&L); and 4,307,254 (CR&L).

The present invention provides a method of separating olefins from paraffins. An advantage of the present process is that the dealkylation of the alkylated aromatic product provides a desired mixture of olefin isomers which are easily separated from the aromatic compounds. This advantage arises from the substantial difference in boiling point between the olefins and the aromatics.

No art is known which discloses the skeletal isomerization of olefins by the alkylation and dealkylation of aromatic compounds therewith. The reaction of olefins with aromatic compounds in the presence of paraffins, separation of the alkylated material, dealkylation of the alkylated material and recovery of skeletally isomerized olefins is not disclosed in the art.

SUMMARY OF THE INVENTION

Broadly, the invention is an olefin skeletal isomerization process for $C_4$ to $C_{15}$ olefins by the reaction of at least one $C_4$ to $C_{15}$ olefin, having a first skeletal distribution, with aromatic compounds under alkylation conditions to produce an alkylated aromatic product, dealkylation of the alkylated aromatic product under dealkylation conditions to produce a dealkylated product comprising said aromatic compounds and olefins corresponding to the olefins in the alkylation and having a second skeletal distribution different than said first skeletal distribution. The olefins fed to the alkylation are isomerized during the alkylation/dealkylation.

The term "skeletal distribution" means the relative composition of the branched to linear isomers of a given olefin. For example, a $C_4$ feed to the alkylation reaction may contain only butene-1 and butene-2, thus its skeletal distribution is o % branched olefins and 100% linear olefins and after the dealkylation there is 50% tert-butylene and the balance butene-1 and butene-2, thus the skeletal distribution of the dealkylated olefins is 50% branched and 50% linear.

The alkylation reaction is preferably carried out under conditions to achieve substantially 100% conversion of the olefins present. Since the olefins are usually present as part of an aliphatic stream, containing paraffins and olefins, the alkylation serves to also separate the alkenes from the remainder of the stream. During the alkylation step, the alkylated aromatic compounds may contain both branched and linear alkyl groups due to the skeletal rearrangement of alkyl groups depending on the alkylation temperature even if only linear olefins are present in the feed.

Acidic catalysts are employed in both the alkylation and the dealkylation steps. Molecular sieves are preferred catalysts for both reactions and zeolites more preferred.

The aromatic compounds from the dealkylation may be recovered and recycled to the alkylation unit to repeat the process. Similarly linear olefins may be recovered and recycled to either the alkylation reaction or dealkylation reaction. One method of recovering the tert-olefins which comprise a part of isoolefins and to separate said tert-olefins from the olefin mixture is to contact the mixture of olefins with a $C_1$ to $C_8$ alcohol to selectively react the tert-olefins to form ethers as described hereinabove. The unreacted olefins from this reaction are easily separated from the ethers for recycle to the alkylation reaction or otherwise employed.

The alkylation and dealkylation reactions may either one or both be carried out in straight pass fixed beds or in catalytic distillation reactors using suitable acidic catalysts such as Al containing materials e.g. alumina and molecular sieves including zeolites. The dealkylation of the alkylate may be carried out using the same or similar catalyst to the alkylation, i.e. acidic catalyst, such as a zeolite. The dealkylation conditions are more severe than the alkylation conditions but in both reactions there may be some reverse reaction. Hence, the reactions carried on by catalytic distillation are advantageous because the reaction products are concurrently separated from the inerts and the distillation can be operated to hold the reactant feed within the catalytic distillation structure bed (in the case of the alkylation the aromatic is maintained in the catalyst zone and the alkylated product removed and in the case of the dealkylation the alkylate product is held in the catalyst zone and the aromatic and olefins removed).

In one embodiment the aromatic alkylation reaction is carried out in a catalytic distillation reactor using a feed that contains paraffins, linear olefins and/or branched olefins using zeolite catalyst wherein a portion of the olefins, up to about 100% conversion of olefins to alkyl aromatics whereby the paraffins and a portion of the excess aromatics are separated from the alkylated products by distillation within the distillation reactor. The separated mixture composed of the alkylated aromatic products and a portion of aromatics is passed through a fixed bed catalytic dealkylation reactor to produce branched olefins. The branched olefin content in the olefin product has been found to equal or higher than that in a conventional olefin isomerization.

In another embodiment the dealkylation of a tert-alkyl aromatic compound is carried out in a catalytic fixed bed reactor. When the dealkylation temperature is relatively low, the olefin product is mostly composed of branched olefin, indicating that there is little isomerization of branched olefin to linear olefin or skeletal rearrangement of tert-alkyl group of the starting alkyl aromatic compound to linear alkyl group. However, as the dealkylation temperature is raised, the linear olefin content in the olefin product was increased steadily, indicating the increased skeletal isomerization of tert-olefin to linear olefin as well as the skeletal isomerization of tert-alkyl group to linear alkyl group.

Undealkylated material is preferably separated from the olefins and returned to the dealkylation zone and the aromatics separated from the olefins and returned to the alkylation zone.

DETAILED DESCRIPTION OF THE INVENTION

Reactants

The olefins are preferably $C_4$ to $C_{10}$ olefins, more preferably $C_4$ to $C_8$ olefins, including normal and iso forms thereof. For example, suitable olefins are butenes, isobutene, 1-pentene, 1-hexene, 2-hexene, 2,3-dimethyl-1-pentene, 1-octene, 1-nonene and 1-decene, dodecene and the like. As described above a special case uses a feed, high in linear olefins which are isomerized during the process to the corresponding iso forms.

The aromatic compounds are preferably organic aromatic compounds under the pressure conditions of the distillation column reactor. The organic aromatic compounds include hydrocarbons of one or more rings and 6 to 20 carbon atoms which may contain substituents which do not interfere with the alkylation including halogen (Cl, Br, F and I), OH and alkyl, cycloalkyl, aralkyl and alkaryl groups of 1 to 10 carbon atoms. Suitable organic aromatic compounds include benzene, xylene, toluene, phenol, cresol, ethyl benzene, diethyl benzene, naphthalene, indene, phenyl bromide, 1,2-dihydronaphthalene and the like, a preferred group of compounds for use in the present process is benzene, xylene, toluene, phenol, and cresol. A preferred group of compounds for use in the present process is benzene, xylene and toluene. Mixtures of aromatic compounds and mixtures of olefins can be used as the feeds for the present process, as may relatively pure streams of either or both.

Alkylation

In the alkylation the mole ratio of organic aromatic compound to olefin may be in the range of 1:1 to 100:1, preferably 2:1 to 50:1 and more desirably about 2:1 to 10:1.

The alkylation reaction is carried out in the presence of acidic catalysts. The preferred catalysts are zeolite Beta, Y-zeolite, ferrierite, mordenite, ZSM-5, ZSM-11, supported phosphoric acid (SPA), acidic resin, etc.

Dealkylation

The dealkylation of alkylated products may be carried out in the presence of acidic catalysts. The preferred catalysts are molecular sieves, purified acidic natural clays and amorphous alumino-silicates. The preferred molecular sieve catalysts are one, two, or three dimensional medium to large pore size (from 3.50 to 7.6 A°, preferentially from 3.5 to 7.5 A°) sieves such as ferrierite, SAPO-11, SAPO-35, ZSM-5, ZSM-22, ZSM-23, ZSM-57, zeolite beta, pentasil zeolite and zeolite Y.

The dealkylation may be carried out in vapor phase or in the presence of both vapor and liquid by employing both fixed bed and catalytic distillation column reactors. The feeds to the dealkylation reactor can be pure alkylates or mixtures of alkylates and aromatic compounds such as benzene, toluene and xylene or paraffins. Since the dealkylation reaction is endothermic reaction, diluted alkylate is desirable to achieve high conversion unless a multiple reactor system is employed with intermittent reheating or more complex reactors such as tube or sheet plate heat exchanged reactors. The products of dealkylation are olefins and aromatics. The olefin products from the dealkylation are composed of the olefin isomers from which tert-olefins may be selectively reacted with alcohols, water, carboxylic acids or aromatic compounds. The remaining linear olefins are returned to either the alkylation reactor or dealkylation reactor to convert to tert-olefins.

The range of temperature for the dealkylation is from 180° to 550° C., preferably from 200° to 450° C. In general, lower pressure is favored for the dealkylation reaction. The range of pressure is from subambient to 350 psig, preferably from ambient to 150 psig.

The alkyl aromatic compound can be pure or mixtures with various aromatic or paraffinic compounds. Depending on the components in the mixtures of alkyl aromatic compounds, the selection of catalyst and operating conditions, the olefin products are pure or substantially pure tert-olefins, substantially pure linear olefins or mixtures of olefin isomers.

The present alkylation reaction can be carried out from ambient pressure to high pressure, e.g., 1 to 40 atmospheres. In the reactor distillation column the temperature will vary depending on the local composition, i.e., the composition at any given point along the column. Furthermore, the temperature along the column will be as in any distillation column, the highest temperature will be in the bottom and the temperature along the column will be the boiling point of the compositions at that point in the column under the particular conditions of pressure. Moreover, the exothermic heat of reaction does not change the temperature in the column, but merely causes more boil up. However, the temperatures within the column with the above considerations in mind will generally be in the range of 50° C. to critical temperature of the mixture, preferably 70° C. to 300° C. at pressures of 1 to 20 atmospheres If the feed for the dealkylation is composed of various alkyl aromatic compounds whose alkyl groups are composed of tert, sec, iso and n-alkyl groups, the dealkylation can be carried out selectively or nonselectively, depending on the purpose of dealkylation or the application of olefin products. For a given catalyst, lower temperatures are employed for the selective dealkylation of tert-alkyl aromatic compounds to tert-olefins. On the other hand, higher temperatures are employed for the nonselective dealkylation to produce the mixed olefin products containing various olefin isomers. For example, if a part of alkyl aromatic compounds are composed of tert-alkyl group containing compounds, pure or substantially pure tert-olefins can be produced by carrying out the dealkylation at lower temperature. It is important that the dealkylation is not carried out at too high temperatures because the olefin product will contain linear olefins due to the skeletal rearrangement of some of the tert-olefin products or tert-alkyl group of alkyl aromatic compounds. The dealkylation of the remaining unconverted alkyl aromatic compounds at higher temperatures produces mixed olefin product of olefin isomers whose composition is near equilibrium distribution. The optimum temperatures for dealkylation depends on the alkyl group on the alkylate and the catalyst employed. For example, when ferrierite molecular sieve is employed as catalyst for the dealkylation of tert-butyl toluene, it is desired to carry out the dealkylation at temperatures lower than about 570° F. For a given acid catalyst, tert-alkyl aromatic compound can be dealkylated at temperatures lower than the corresponding sec-alkyl aromatic compounds. Tert-alkyl aromatic compounds can be dealkylated over mildly acidic catalysts.

The works of R. M. Roberts and D. Farcasiu discussed above may suggest a reaction mechanisms involved in the conversion of linear olefins to isoolefins via the consecutive alkylation-dealkylation reactions disclosed in this invention. These consecutive reactions can be carried out in one step or two steps. If the alkylation is carried out at higher temperatures and low pressures, both alkylation and dealkylation as well as olefin isomerization can occur simultaneously in the catalytic reaction zone, resulting in the olefin isomers in the reaction products in one step. However, if the alkylation reaction is carried out at lower temperature and high pressure, and the dealkylation is carried out at higher temperature and lower pressure, the same result can be obtained in two steps The products from the dealkylation step are mixtures of isoolefins and linear olefins from which isoolefins (branched olefins) can be separated from linear olefins by existing technologies such as extractive distillation or selective reaction such as etherification. In the selective reaction technique, the separation of isoolefins in the mixtures is achieved by reacting isoolefins with a number of reactants. Since isoolefins are much more reactive than linear olefins, isoolefins in the mixtures can be reacted selectively with alcohols, water, carboxylic acids and aromatics, and then unreacted linear olefins are separated from higher boiling reaction products by simple distillation technique. The recovered linear olefins are recycled back to the alkylation reactor.

When alcohol such as methanol or ethanol is employed for the selective reaction agent for isoolefins, ether such as methyl tert-butyl ether or ethyl tert-butyl ether is the reaction product. These ethers are valuable products, for these ethers have been used for the blending components as oxygenates and octane component for the reformulated gasoline. If isoolefins are desired products, these ethers are dealkylated to isoolefins and alcohols, and isoolefins are separated from alcohols by simple distillation. Therefore, this invention provides a means to convert low RON olefin components in the mixtures to high RON as well as lower high vapor pressure components in gasoline. It is desirable to reduce the olefin and aromatic components in the gasoline due to environmental and other reasons. Ethers are excellent replacement components for this purpose. Therefore, this invention provides a useful technology for the production of MTBE or TAME from the mixed olefin streams.

When aromatic compounds such as benzene, toluene, xylenes or phenols are employed for the selective reaction agents with isoolefins, tert-alkyl aromatic compounds are reaction products. When isoolefins are desired products, these tert-alkyl aromatic compounds are dealkylated in the presence of acidic catalysts. It is important that the dealkylation is not carried out at too high temperatures. If the dealkylation temperature is too high, the olefin product will contain linear olefins.

If the alkyl groups of alkyl aromatic compounds are composed of linear alkyl groups and linear olefins are desired products, the dealkylation is carried out at lowest possible temperature by employing less acidic catalysts.

Straight Pass Reactor

For the fixed bed straight pass alkylation, the olefin and aromatic feeds are premixed prior to entering the catalytic reaction zone. Another technique carrying out this fixed bed alkylation is that olefin feed is divided into several portions and then each portion is fed to the alkylation reactor at the different locations as the aromatic feed flows through the fixed bed reactor. For this fixed bed operation, the reactor effluent stream may be recycled to improve the selectivity and dilute the heat of reaction, because the alkylation reaction is exothermic. The preferred range of the temperature for the alkylation is from 50° to 500° C., preferably from 80° to 300° C. The pressure for the alkylation reactor should be high enough so that a portion of aromatics would exist as liquid form. Therefore, the pressure for the alkylation reactor depends on the temperature and the composition of the feed to the reactor.

Distillation Column Reactor

When the alkylation is carried out by employing the catalytic distillation reactor, a distillation column is loaded with acidic catalysts, and light olefins such as $C_4$ or $C_5$ olefins may be introduced into the distillation tower at the bottom section of tower and aromatics such as toluene or xylene may be introduced into the distillation tower at the top section of the tower, or both olefins and aromatics are introduced at the lower section of the tower depending on the operating condition such as temperature and pressure required for the effective alkylation and separation of paraffins from aromatics or aromatics from the alkylated products. Unreacted paraffins in the olefin containing feed are separated from the reaction mixture as overhead product, and the alkylates (alkylated products) and possibly some of the aromatics are withdrawn at the bottom of the tower as the bottom product. If desired, one may remove a part of the aromatics as the overhead product along with paraffins.

After the dealkylation of alkylate is carried out, the products, olefins and aromatics, are removed from the column as overhead, and unreacted alkylates are recovered as the bottom product to recycle back to the top of the catalyst. The desired conversion per pass is from 10 to 100%, preferentially 30 to 80%.

When the dealkylation is carried out by employing the catalytic distillation column reactor, the column pressure should be high enough so that, at least, a part of feed would exist in liquid form. The product olefins are removed from the catalytic reaction zone as the overhead product. The unconverted alkylates are removed from the bottom of the column and recycled to the top of the catalyst.

When alkylation is carried out in the catalytic distillation mode, the exact location of the olefin feed in the distillation column reactor will depend on the particular feeds and the desired product. In one embodiment the olefin feed to the reactor is preferably made below the catalyst bed thereby allowing mixing of the reactants before contact with the catalyst bed. In another embodiment the olefin feed to the reactor is preferably made above the catalyst bed.

The aromatic feed may be added at any point in the distillation column reactor, however, preferably it is added below the fixed bed or to the reflux as makeup, depend on its boiling point. Preferably there is a large excess of the aromatic to the olefin in the reactor in the range of 2 to 100 moles of aromatic per mole of olefin, that is the net molar feed ratio of aromatic compound to olefin may be close to 1:1, although the catalytic distillation system is operated so as to maintain a substantial molar excess of aromatic compound to olefin in the reaction zone. The alkylated product is the highest boiling material and is separated in the lower portion of the column usually as bottoms. The organic aromatic compound can be the second highest boiling or third highest boiling component.

Very large molar excesses of aromatic compounds require a very high reflux ratio in the column, and a low unit productivity. Hence, the correct ratio of aromatic compound to olefin must be determined for each combination of reactants as well the acceptable olefin content in either the overhead or alkylation product.

The length of the catalyst bed in the column, particularly that portion wherein the reactants are in contact and the reaction occurs, depends on the reactants, location of the olefin feed and the acceptable unreacted olefin in the streams leaving the tower. Some degree of testing will be required for each set of reactants and parameters of stream purity following present disclosures.

The advantages of present alkylation carried out in the catalytic distillation mode are derived from the continuous wash-off of the coke or coke precursors on the catalyst surface, resulting in much longer catalyst life, the natural separation of products in the catalytic reaction zone, the steadier flow of the reactants to the catalytic reaction zone, better transport of materials between the bulk phase and the reaction zone, and better temperature control caused by dynamic vapor-liquid equilibrium and vapor traffic then the traditional fixed bed process.

The alkylate products are composed of a number of different alkyl groups. For example, when n-butenes are olefins for the alkylation, the alkyl groups on the alkylated aromatic compounds are mostly sec-butyl and tert-butyl groups. The degree of isomerization of alkyl group depends on the temperature. For example, if the alkylation is carried out at temperatures lower than about 400° F. with molecular sieve catalysts, then alkylation products contain a small amount of tert-butyl aromatic compounds. When n-pentenes are used, the alkyl groups are isomers of $C_5$ such as sec-pentyl, 3-methyl-butyl, tert-amyl, etc. If a mixed $C_5$ stream such as TAME raffinate is used for the alkylation, the paraffin components in the mixed feed can easily be separated from the alkylate and can serve as feed stock for the steam cracker for the ethylene production or the paraffin skeletal isomerization, because it contains little or no olefins.

In some reactions in the distillation column reactor, the olefin will be a higher boiling material than the aromatic hydrocarbon, e.g., $C_8+$ olefins. In such instances in a catalytic distillation reaction any unreacted olefin will appear in the bottoms alkylation product, although a side draw may be used to reduce such material in the product to an insignificant level. However, operating the reaction with far less than a stoichiometric amount of olefin in the reaction zone, as described, will normally keep the olefin level in the bottoms low or entirely eliminated.

Catalysts

Molecular sieves are porous crystalline alumina-silicate materials. Zeolites are one of the typical examples which are composed of silicon and aluminum atoms each surrounded by four oxygen atoms to form a small pyramid or tetrahedron (tetrahedral coordination). The term molecular sieve can be applied to both naturally occurring zeolites and synthetic zeolites. Naturally occurring zeolites have irregular pore size and are not generally considered as equivalent to synthetic zeolites. In the present invention, however, naturally occurring zeolites are acceptable so long as they are substantially pure. The balance of the present discussion shall be directed to the synthetic zeolites with the understanding that natural zeolites are considered equivalent thereto as indicated above, i.e. in so far as the natural zeolites are the functional equivalents to the synthetic zeolites.

The particulate molecular sieves or other catalysts may be employed by enclosing them in a porous container such as cloth, screen wire or polymeric mesh for use in catalytic distillation. The material used to make the container must be inert to the reactants and conditions in the reaction system. The cloth may be any material which meets this requirement such as cotton, fiber glass, polyester, nylon and the like. The screen wire may be aluminum, steel, stainless steel and the like. The polymer mesh may be nylon, teflon or the like. The mesh or threads per inch of the material used to make the container is such that the catalyst is retained therein and will not pass through the openings in the material. Particles of about 0.15 mm size or powders may be used and particles up to about ¼ inch diameter may be employed in the containers.

The container employed to hold the catalyst particles may have any configuration, such as the pockets disclosed in the commonly assigned patents above or the container may be a single cylinder, sphere, doughnut, cube, tube or the like.

Each container containing a solid catalytic material comprises a catalyst component. Each catalyst component is intimately associated with a spacing component which is comprised of at least 70 volume % open space up to about 95 volume % open space. This component may be rigid or resilient or a combination thereof. The combination of catalyst component and spacing component form the catalytic distillation structure. The total volume of open space for the catalytic distillation structure should be at least 10 volume % and preferably at least 20 volume % up to about 65 volume %. Thus desirably the spacing component or material should comprise about 30 volume % of the catalytic distillation structure, preferably about 30 volume % to 70 volume %. One suitable spacing material is open mesh knitted stainless wire, known generally as demister wire or an expanded aluminum. Other resilient components may be similar open mesh knitted polymeric filaments of nylon, teflon and the like. Other materials such as highly open structures foamed material, e.g., ceramic or metal foam monolith structures (rigid or resilient) may be formed in place or applied around the catalyst component. In the case of larger catalyst components such as from about ¼ inch to ½ pellets, spheres, pills and the like, each such larger component may be individually intimately associated with or surrounded by the spacing component as described above. It is not essential that the spacing component, entirely cover the catalyst component. It is only necessary that the spacing component intimately associated with the catalyst component will act to space the various catalyst components away from one another as described above. Thus, the spacing component provides in effect a matrix of substantially open space in which the catalyst components are randomly but substantially evenly distributed.

One catalytic distillation structure for use herein comprises placing the molecular sieve particles into a plurality of pockets in a cloth belt, which is supported in the distillation column reactor by open mesh knitted stainless steel wire by twisting the two together in a helical form. This allows the requisite flows and prevents loss of catalysts. The cloth may be any material which is inert in the reaction. Cotton or linen is useful, but fiber glass cloth is preferred.

Figure 4:
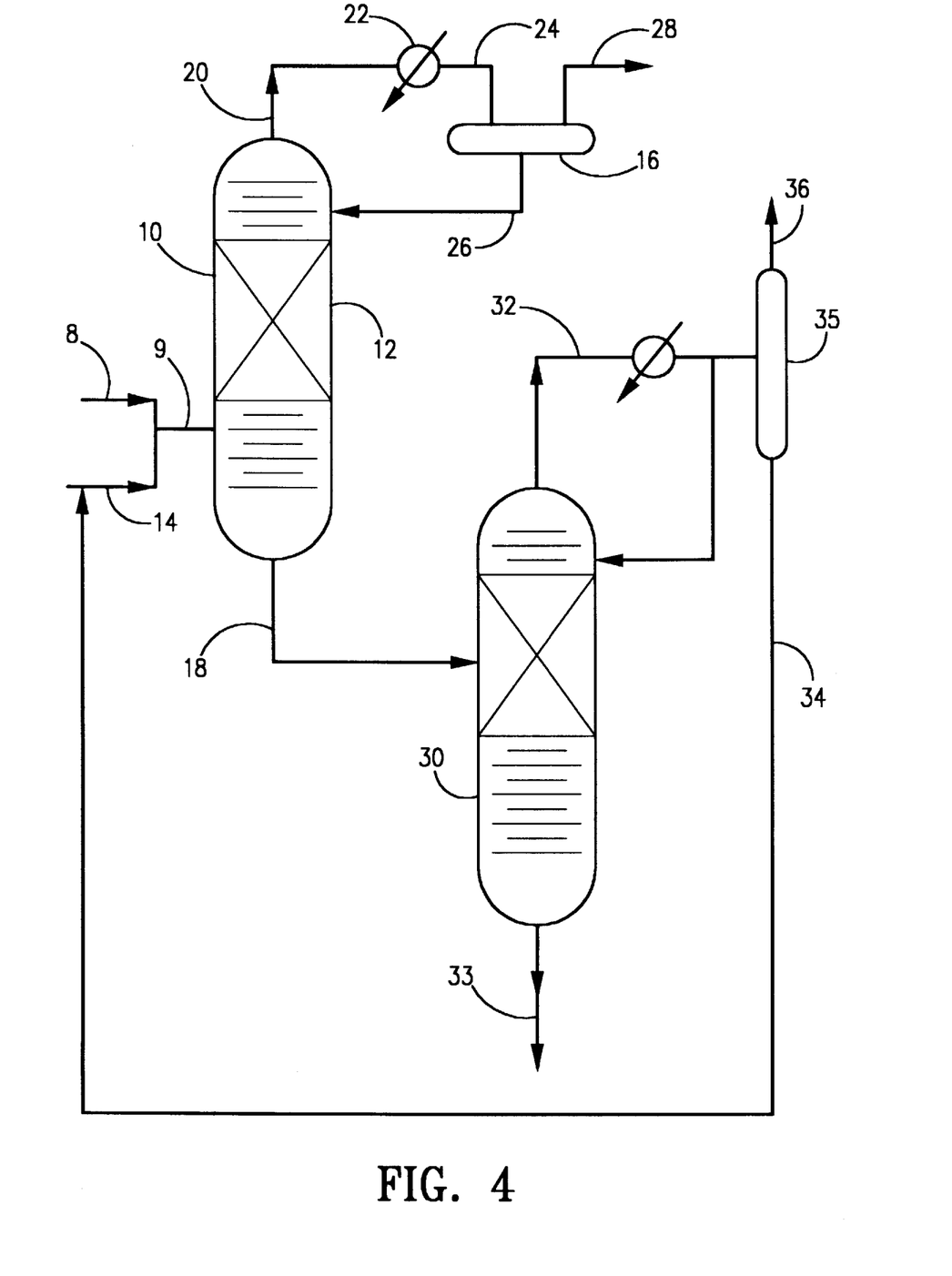
FIG. 4 is a flow chart of the present invention for separation of isoolefins.

FIG. 4 illustrates one embodiment of the present invention, i.e., the production of high purity isobutene by alkylating benzene with isobutene from a $C_4$ stream containing predominately n-butene, isobutene and $C_4$ alkanes. Referring to the drawing, distillation column reactor 10 is divided into three sections. In the middle section the catalyst packing (catalytic distillation structures) 12 is positioned as described, using a Y-zeolite ferrierite deposited in the pockets of fiber glass belts and formed into a helix with stainless steel mesh as described.

The lower portion of the column is a conventional distillation column configuration. Make-up benzene is conveniently added via line 14. The olefin containing feed 8 is mixed with the benzene and fed to the column via 9 just below the catalyst packing 12 for better mixing. The reaction is exothermic and initiated by contacting the two reactants in the catalyst packing. The alkylated products are higher boiling than benzene and the $C_4$ feed, and are recovered via 18 as a bottoms product. The feed of $C_4$'s is adjusted such that there is a molar excess of benzene in the reactor. In addition to the $C_4$ alkanes and benzene and other lights go off as overhead 20. The overhead is passed to condenser 22 which is operated to condense substantially all of the benzene which passes via 24 to accumulator 16 and hence, by reflux via 26 to column 10. The benzene used in the reaction and lost with the lights, primarily $C_4$ alkanes (which exit accumulator 16 via 28) is made up by fresh benzene feed 14.

The bottoms contain a mixture of isobutene alkylated benzene and primary and secondary butyl benzene which passes via 18 to dealkylation unit 30, which is a catalytic distillation column operated to concurrently dealkylate the alkylate and fractionate benzene and butenes as overhead 32 and the heavies as a bottoms product 33. In this embodiment the benzene is separated from the olefin in column 35 and returned via 34 to the feed 14 to column 10. The olefins are recovered as overheads 36.

Figure 1:
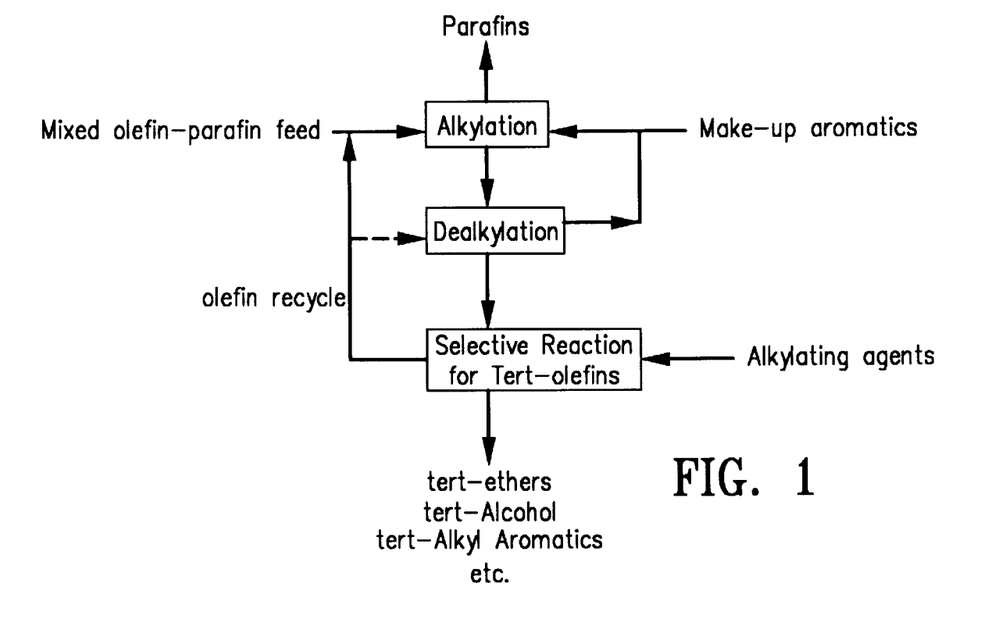
FIG. 1 is schematic representation of one embodiment of the alkylation, dealkylation and olefin recovery.

FIG. 1 is a flow chart showing in graphic form the path of the reactants, products and by-products through each of several reactions possible in the system, including the separation and recovery of the isoolefins from the primary olefins.

Figure 2:
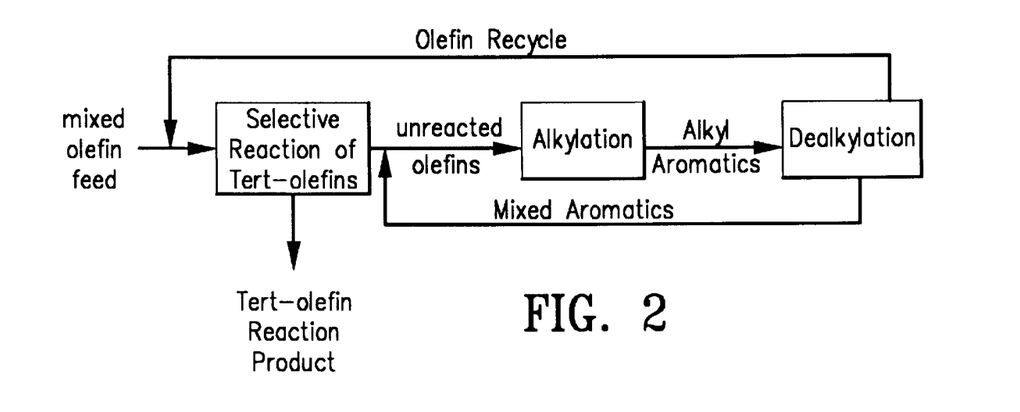
FIG. 2 is a schematic representation of one embodiment of a selective reaction for tert-olefins followed by the alkylation/dealkylation.

FIG. 2 is a flow chart showing the treatment of unreacted olefins from a tertiary olefin reaction according to the present alkylation/dealkylation.

Figure 3:
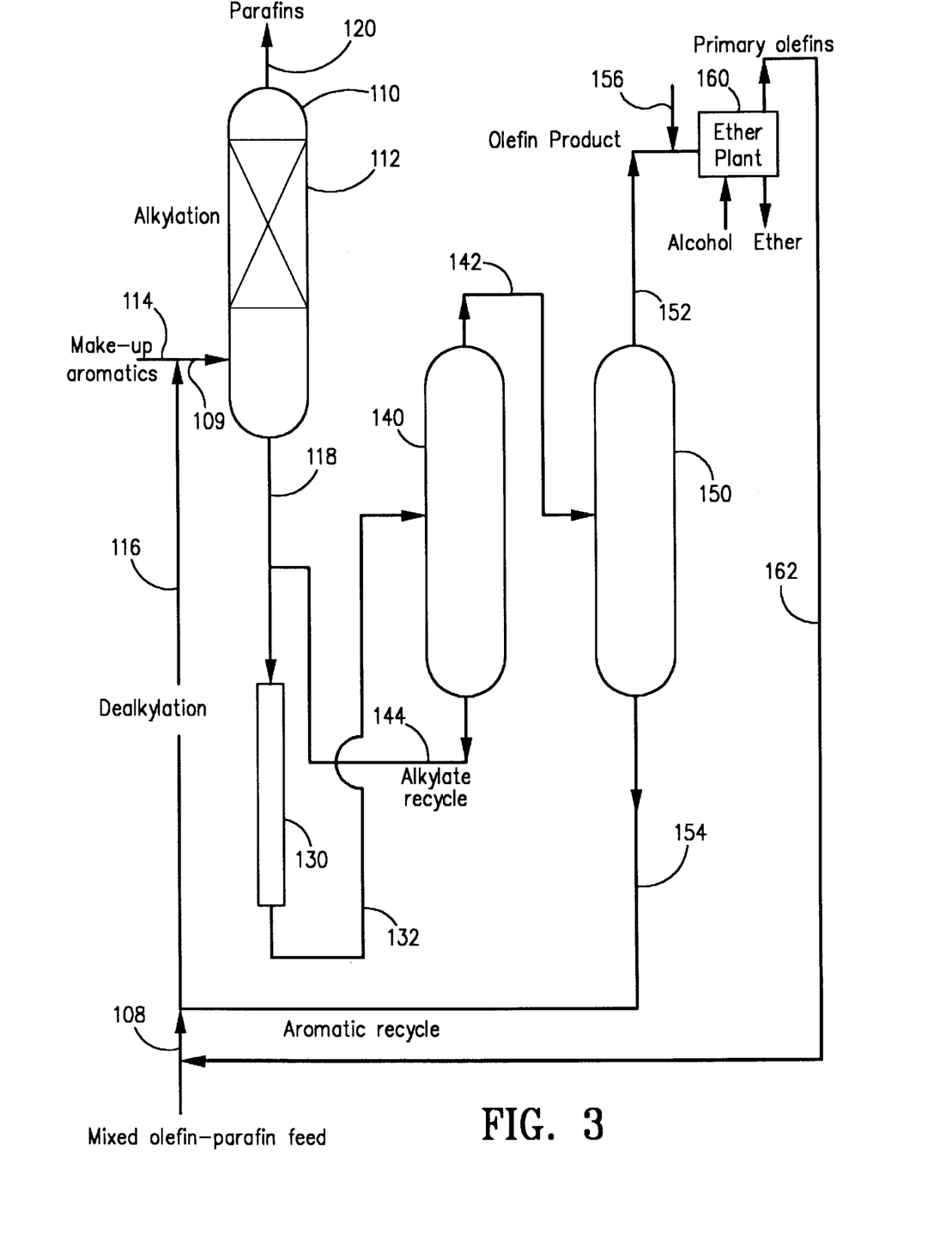
FIG. 3 is schematic representation of one embodiment of the alkylation, dealkylation and isoolefin recovery by selective etherification of the isoolefin.

FIG. 3 illustrates an embodiment of the present invention, i.e., the production of high purity isobutene by alkylating toluene with isobutene from a $C_4$ or $C_5$ stream containing predominately n-butene, isobutene and $C_4$ alkanes or the corresponding $C_5$ primary and isoolefins. Referring to the drawing, distillation column reactor 110 with the middle section containing the catalyst packing (catalytic distillation structures) 112 positioned as described, using beta zeolite deposited in the pockets of fiber glass belts and formed into a helix with stainless steel mesh as described.

The lower portion of the column is a conventional distillation column configuration. Make-up toluene is conveniently added via line 114. The olefin containing feed 108 is mixed with the toluene recycle 154 and the non isoolefin recycle 162 and fed to the column via 109 below the catalyst packing 112 for better mixing. The reaction is exothermic and initiated by contacting the two reactants in the catalyst packing. The alkylated products are higher boiling than toluene and the $C_4$ or $C_5$ feed and are recovered via 118 as a bottoms product. The feed of $C_4$ or $C_5$ is adjusted such that there is a molar excess of toluene to olefin in the reactor. In addition to the $C_4$ or $C_5$ alkanes, other lights and some toluene go off as overhead 120. The overhead 120 is passed to a condenser (not shown) to condense substantially all of the toluene which is returned to column 110 as reflux.

The bottoms in column 110 contain a mixture of alkylated toluene (the olefins are substantially 100% converted) which pass via 118 to dealkylation unit 130, which is a fixed bed straight pass reactor operated to concurrently dealkylate the toluene alkylate. The total dealkylation product is passed via line 132 to distillation column 140 where the undealkylated material is separated and recycled via line 144 to the dealkylator 130. The toluene and olefins are recovered as overhead via line 142 to distillation column 150, where the aromatic are recovered as a bottoms via line 154 and recycled to the alkylation column 110. In this embodiment the olefins are passed to an ether plant 160 where the isoolefins are preferentially reacted with alcohol, such as methanol to form MTBE or TAME. Make up olefin feed may be added via line 156.

The ether plant may be any of those known in the art. The present system has a double benefit when used in conjunction with an ether plant. First because there is a conversion of linear olefins to isoolefins the efficiency of the ether unit is increased, two ways, first by conversion of the linear olefins in the make-up feed and conversion of the recycled linear olefins from the ether plant to the present system. The second benefit is the removal of potential poisons for the etherification catalyst. For example, propionitrile, which is a cumulative poison to acidic resin catalysts used in etherification, and dimethylsulfide will either pass through the alkylation zone and exit with the alkanes or react on the alkylation catalyst and be removed during the regeneration. Unreacted olefins from the ether plant may be recycled to the mixed olefin fee via line 162.

Such conventional items as valves, reboilers, slip streams, etc. are not shown, but would be obvious expedients to those setting up such equipment.

EXAMPLES

Example 1

Control A 4 lbs. of the commercial ferrierite 1/16" extrudate catalyst (P1) was packed in 2.5" diameter tube. The catalyst bed length was 4'. Skeletal isomerization of n-pentenes in a mixed $C_5$ hydrocarbons (TAME raffinate) was carried out in the traditional fixed bed operation by passing the hydrocarbon vapor over the catalyst downflow. The TAME raffinate was composed of 4.56 wt % $C_3$–$C_4$s, 32.14 wt % n-pentenes, 4.36 wt % isoamylene (2-methyl-2-butene and 2-methyl-1-butene), 0.94 wt % 3-methyl-1-butene, 50.27 wt % isopentanes, 6.45 wt % n-pentane, 1.28 wt % +$C_6$ and others. The isomerization results at 41 hours on stream is listed in Table 1.

Control B

A similar experiment at a different condition was carried out with a different feed. The mixed $C_5$ feed was composed of 1.29 wt % $C_3$–$C_4$s, 66.04 wt % n-pentenes, 9.86 wt % isoamylene (2-methyl-2-butene and 2-methyl-1-butene), 2.87 wt % 3-methyl-1-butene, 3.51 wt % isopentanes, 14.63 wt % n-pentane, 1.80 wt % +$C_6$ and others. The isomerization results at 31 hours on stream is listed in Table 1.

Example 2

Control 4.1 lb of the commercial ferrierite 1/16" extrudate catalyst (P1) was packed in 2.5" diameter tube. The catalyst bed length was 4'. Skeletal isomerization of n-butenes in a mixed $C_4$ hydrocarbons (raffinate 2) was carried out in the traditional fixed bed operation by passing the hydrocarbon vapor over the catalyst downflow. The MTBE raffinate feed was composed of 0.03 wt % $C_3$, 4.64 wt % isobutane, 22.85% n-butane, 1.35 wt % isobutylene, 70.95 wt % n-butenes, 0.18 wt % +$C_5$ and others. The isomerization results at about 49 hours on stream is listed in Table 3.

Example 3

M-xylene was alkylated with a $C_5$ TAME raffinate over a commercial zeolite Beta catalyst (6 g, 10–20 mesh in a 0.5" diameter×10" long stainless steel tube) at 420° F. under 100 psig pressure. The feed was prepared by mixing m-xylene with a $C_5$ TAME raffinate to have a xylene/olefin ratio of 4.90. The composition of the TAME raffinate was 0.07 wt % $C_{3s}$, 2.92 wt % butenes, 0.54 wt % butanes, 33.33 wt % n-pentenes, 4.64 wt % isoamylenes (2-methyl-2-butene and 2-methyl-1-butene), 0.92 wt % 3-methyl-1-butene, 0.72 wt % cyclopentene, 48.25 wt % isopentane, 7.56 wt % n-pentane and 1.05 wt % $C_6$+/unknown. The alkylation was carried out at 300°–350° F. and 100 psig pressure with 12 WHSV feed rate. The conversion of total olefins in the feed was a range of 97.7 to 100%. A composite product from the alkylation reaction of xylene with a mixed $C_5$ olefins was concentrated by distilling off nonaromatics and some of the excess xylene to prepare the feed for the dealkylation. The feed composition for the dealkylation was 28.53 wt % alkylate and 71.47 wt % xylene. Five different commercial catalysts (6 g and 10 to 20 mesh) were loaded in a stainless steel reactor (0.5" diameter×10" long) for the dealkylation reaction of the above feed. The results of the dealkylation are listed in the Table 1.

Example 4

Alkylation of toluene with a mixed $C_4$ stream was carried out by utilizing a catalytic distillation reactor. The composition of the mixed $C_4$ stream was 0.98% isobutane, 0.42% isobutylene, 45.33% n-butane, 31.98% trans-2-butene, 16.10% cis-2-butene and 5.19% +$C_5$. The height of the catalytic distillation column was 25' and the inside diameter of the column was 1". A commercial zeolite Beta (0.46 lb and 16" extrudates) was packed in the specially designed permeable containers and loaded in the mid section of the distillation column. The catalyst bed length was 10'. The top and bottom sections (each 7.5') of the catalyst were packed with ceramic saddles.

The range of the operation condition of the catalytic distillation was 448°–479° F. column temperature, 245–270 psig overhead pressure and 13–24 WHSV feed rate. Toluene to olefin mole ratio in the feed was ranged from 4.5 to 6.2. The paraffin components in feed, a very small amount of unreacted olefins and about 60–80% of unreacted toluene are removed from the top of the column as the overhead product. The alkylate products and about 20–40% remaining unreacted toluene are removed from the reboiler at the bottom of the column as the bottom products. The results of the alkylation are listed in Table 2. A composite product, whose composition was 0.97 wt % nonaromatics, 36.93% aromatics (benzene, toluene and xylenes), 61.86 wt % various butyltoluene isomers (mono, di and tributyltoluene), and 0.42 wt % heavies, was dealkylated over various molecular sieve catalysts. The alkyl group on butyltoluene is composed of linear and branched butyl groups, but mostly sec-butyl group. The results are listed in Table 3.

Example 5

Dealkylation of tert-butyl toluene is carried out by using a feed composed of 64.5% tert-butyl toluene and 35.41% toluene. A commercial ferrierite catalyst (4.78 g and 10 to 20 mesh) was loaded in a stainless steel reactor (0.5" diameter× 10" long) for the dealkylation reaction of the above feed. The results are listed in Table 4.

TABLE 1

| | n-$C_5$ Olefins Skeletal Isomerization | | Dealkylation of Pentylxylene Alkylates | | | | |
|---|---|---|---|---|---|---|---|
| EXAMPLE | Control 1A | Control 1B | 3 | | | | |
| Catalyst | P1 | P1 | P1 | P4 | EZ | UP | P3 |
| Temp, °F. | 750 | 670 | 650 | 550 | 600 | 600 | 550 |
| Pressure, psig | 10 | 15 | 25 | 30 | 30 | 30 | 30 |
| Flow Rate, WHSV | 7 | 7 | 7 | 10 | 6.5 | 7 | 7 |
| Conversion, % | 71.7** | 30.5** | 52.9 | 37.9 | 43.4 | 53.4 | 42.8 |
| i-$C_5^{-*}$/n-Pentenes | 2.56 | 0.798 | 3.04 | 4.04 | 1.06 | 2.93 | 2.33 |
| i-$C_5^-$ * % $C_5^-$ Product | 68.0 | 43.1 | 70.9 | 75.1 | 49.2 | 72.4 | 68.2 |
| i-$C_4^-$ % in $C_4^-$ Product | 40.7 | 31.8 | 41.8 | 42.2 | 17.5 | 20.8 | 24.2 |
| Product Distribution, wt % | | | | | | | |
| $C_1$–$C_3$ | 1.2 | 0.1 | 3.9 | 2.1 | 0.9 | 2.1 | 1.5 |
| $C_4$ | 5.3 | 1.3 | 11.7 | 15.0 | 15.3 | 22.3 | 22.9 |
| $C_5$ | 90.9 | 98.0 | 78.9 | 70.1 | 83.8 | 59.3 | 69.3 |
| +$C_6$ | 2.6 | 0.6 | 5.5 | 12.7 | tr | 16.3 | 6.3 |
| $C_4^-$ % in $C_4$ Product | 86.6 | 79.8 | 93.5 | 83.2 | 79.2 | 63.4 | 59.7 |
| $C_5^-$ % in $C_5$ Product | 37.1 | 80.8 | 80.2 | 98.7 | 85.7 | 77.8 | 75.7 | i-$C_5^-$ = 2-M-B-2 + 2-M-B-1
P1 = Ferrierite (G1), EZ = Y-Zeolite, UP = Zeolite Beta(UE), P3 = Zeolite Beta (QQ)
P4 = Ferrierite (G2)
** Conversion of n-$C_5^-$

TABLE 2

Alkylation of Toluene with a Mixed $C_4$ Feed
(Catalytic Distillation Mode)

| Column temp, °F. | 448–461 | 459–474 | 455–483 | 455–479 |
|---|---|---|---|---|
| Reboiler temp, °F. | 600 | 595 | 607 | 609 |
| OVHD press, psig | 270 | 245 | 255 | 255 |
| Column p.d., psig | 2.5 | 2.5 | 2.5 | 2.5 |
| Feed rate, WHSV | 13 | 13 | 13 | 24.1 |
| Toluene/butene mole ratio | 6.21 | 5.07 | 4.47 | 6.19 |
| Hours on stream | 276 | 456 | 612 | 804 |
| Butene Conversion, % | 99.5 | 99.3 | 99.2 | 95.4 |
| Monoalkylate in alkylate, wt % | 98.1 | 95.3 | 96.5 | 98.4 |

TABLE 3

| Example | n-$C_4$ Olefins Skeletal Isom 2 | Deaklylation of Butyltoluene 5 | | | | | | | |
|---|---|---|---|---|---|---|---|---|---|
| Catalyst | P1 | P1 | P2 | U1 | U1 | P3 | UP | UC | PM |
| Temp, °F. | 800 | 750 | 750 | 750 | 650 | 700 | 600 | 650 | 670 |
| Pressure, psig | 10 | 10 | 10 | 10 | 10 | 10 | 10 | 10 | 10 |
| Flow Rate, WHSV | 12 | 4 | 7 | 4 | 4 | 7 | 7 | 20 | 16 |
| Conversion, % | 49.7** | 49.7 | 40.7 | 64.2 | 51.5 | 81.2 | 73.9 | 59.1 | 47.1 |
| i-$C_4^=$ % in $C_4^=$ Product | 45.4 | 44.0 | 44.1 | 45.2 | 47.6 | 20.3 | 48.1 | 44.8 | 7.83 |
| i-$C_5^=$* % in $C_5^=$ Product | 1.94 | 2.75 | 2.70 | 2.72 | 3.32 | 2.96 | 3.64 | 3.24 | 1.41 |
| Product Distribution, wt % | | | | | | | | | |
| $C_1^=$ $C_3$ | 0.5 | 7 | 10.6 | 21.7 | 15.7 | 8.1 | 16.4 | 14.2 | 2.4 |
| $C_4$ | 93.5 | 83.3 | 76.1 | 41.4 | 39.3 | 63.2 | 40.8 | 40.7 | 85.8 |
| $C_5$ | 1.2 | 5.2 | 6.6 | 17.6 | 21.2 | 17.5 | 22.7 | 22.8 | 11.0 |
| +$C_6$ | 4.8 | 4.5 | 6.7 | 19.3 | 23.8 | 11.2 | 20.1 | 22.1 | 0.8 |
| $C_4^=$ in $C_4$ Product | 69.9 | 90.8 | 85.9 | 29.8 | 20.6 | 73.7 | 13.5 | 41.1 | 88.8 |
| $C_5^=$ in $C_5$ Product | 81.0 | 97 | 97.7 | 35.7 | 25.0 | 73.7 | 16.3 | 50.9 | 51.7 |

*Isoamylene = 2-M-B-1 + 2-M-B-2
PI = Ferrierite (G1), P2-Ferrierite (N), U1 = ZSM-5, P3 = Zeolite Beta (QQ), UP = Zeolite Beta (UE), UC = Pentasil Zeolite, PM = Zeolite Beta(S)
**n-$C_4^=$ Conversion

TABLE 4

Dealkylation of 4-tert-Butyltoluene Alkylate

| Temp, °F. | 450 | 500 | 550 | 600 | 650 | 700 |
|---|---|---|---|---|---|---|
| Pressure, psig | 40 | 40 | 40 | 40 | 50 | 50 |
| Flow Rate, WHSV | 10 | 10 | 10 | 10 | 10 | 10 |
| Conversion, % | 23.5 | 26.2 | 28.8 | 33.4 | 59.8 | 71.6 |
| i-Butene % in $C_4^=$ | 93.9 | 94.8 | 94.7 | 84.8 | 74.4 | 67.2 |
| Therm Eq Comp, % | 61.8 | 59.3 | 57.4 | 55.8 | 53.8 | 52.3 |

The control experiments were carried out for the skeletal isomerization of linear olefins in the control example 1 and 2. When the isomerization of linear $C_4$ and $C_5$ olefins was carried out in vapor phase by employing a commercial ferrierite catalyst in the traditional fixed bed operation, there were dramatic changes in activity and selectivity at the beginning of the reaction as others stated in the published papers and patents, because of the coke formation on the strong active sites. The skeletal isomerization of linear $C_4$ and $C_5$ olefins became effective at relatively high temperature, >750° F.

When the conversion of linear olefins to isoolefins was carried out according to this invention, there were marked differences in the reaction temperature from the traditional vapor phase fixed bed olefin skeletal isomerization, allowing wider range of operation temperature for this invention. This translates into longer catalyst cycle time. Because of the cleaning effect by the high boiling aromatic compounds in feeds during the alkylation or dealkylation, it was possible to keep the catalyst surface and pores cleaner for a longer time. The active sites and pores on the catalysts were kept cleaner from the coke deposition. Therefore, the catalysts were able to sustain high activities for longer time.

Surprisingly, dealkylation reaction of the alkylates was effective at the temperatures much lower than the temperature (<750° F.) required for the olefin skeletal isomerization in the fixed bed operation. The fact that the dealkylation reaction can be carried out at a temperature lower than olefin skeletal isomerization for a given catalyst has very important implication for the production of isoolefins or isoolefin derivatives. Since the equilibrium concentration of isoolefins decreases with temperature, the conversion of linear olefins to isoolefins carried out according to this invention results in higher isoolefin yields in TABLES 1 and 3. The advantage of this invention over the conventional olefin skeletal isomerization process can be clearly understood. Not only the isoolefin components in the product streams in this invention are higher than the conventional olefin skeletal isomerization, but also the product streams from this invention have higher concentrations of olefins, resulting in desirable isoolefin streams for the down stream processing. For example, in the production of ethers such as MTBE or TAME, higher yield of ethers can be obtained for a given size unit. Linear olefins in the products can be converted to isoolefins after removal of isoolefins by selective reaction of isoolefins and by recycling to alkylation reactor, because the paraffin components in the product stream are sufficiently low. However, this is not true for the conventional olefin skeletal isomerization processes, because the olefin concentration in the raffinate stream from the isoolefin recovery reactor (the selective reactor) is too dilute. The higher boiling alkylated products can easily be dealkylated to olefins and aromatics. The unconverted alkylates can be recovered by the conventional method such as simple distillation and recycled and the aromatics separated from $C_4$ or $C_5$ hydrocarbons by conventional distillation or stripping technique and recycled back to the alkylation reactor.

When tert-alkyl benzene such as tert-butyltoluene is dealkylated by using ferrierite catalyst (P1) at lower temperatures, the olefin products are substantially pure isobutylene as shown in TABLE 4. However, when the dealkylation was carried out at higher temperature, the tert-olefin products were diluted increasingly with other olefin isomers.

This invention also can be utilized to improve the octane of FCC gasoline and lightly reformed naphtha gasoline in one step. Instead of carrying out alkylation and dealkylation separately, alkylation, dealkylation and olefin isomerization may be simultaneously carried out in a catalytic distillation column in which an acidic catalyst is loaded. The $C_4$–$C_8$ olefins in the gasoline can effectively be converted to mixtures of olefin isomers. The gasoline feed is fed to the mid section of the catalytic distillation tower. The exact position of feed position on the tower can be varied by the composition of the gasoline to obtain the best RON improvement. The overhead and bottom products from the distillation tower are combined to produce improved gasoline.

The invention claimed is:

1. A process for the skeletal isomerization of $C_4$ to $C_{15}$ olefins comprising, (a) reacting at least one $C_4$ to $C_{15}$ olefin having a first skeletal distribution with aromatic hydrocarbons under alkylation conditions to produce an alkylated aromatic product, and (b) dealkylating the alkylated aromatic product under dealkylation conditions to produce a dealkylated product comprising said aromatic hydrocarbons and olefins corresponding to the olefins in the alkylation and having a second skeletal distribution different than said first skeletal distribution.

2. The process according to claim 1 wherein said olefin is at least one $C_4$ to $C_8$ olefin.

3. The process according to claim 1 wherein $C_4$ olefin is present.

4. The process according to claim 1 wherein $C_5$ olefin is present.

5. The process according to claim 1 wherein said alkylation is carried out under conditions to obtain 10–100% conversion of the olefin present.

6. The process according to claim 5 wherein said alkylation is carried out under conditions to obtain 30–100% conversion of the olefin present.

7. The process according to claim 1 wherein said alkylation is carried out in the presence of an acidic catalyst.

8. The process according to claim 7 wherein said acidic catalyst comprises a molecular sieve.

9. The process according to claim 7 wherein said acidic catalyst comprises a zeolite.

10. The process according to claim 1 wherein said dealkylation is carried out in the presence of an acidic catalyst.

11. The process according to claim 10 wherein said acidic catalyst comprises a molecular sieve.

12. The process according to claim 10 wherein said acidic catalyst comprises a zeolite.

13. A process for the skeletal isomerization of $C_4$ to $C_{15}$ olefins comprising (a) reacting at least one $C_4$ to $C_{15}$ olefin having a first skeletal distribution with aromatic hydrocarbons under alkylation conditions in the presence of an acidic catalyst to produce an alkylated aromatic product, and (b) dealkylating the alkylated aromatic product under dealkylation conditions in the presence of an acidic catalyst to produce a dealkylated product comprising said aromatic hydrocarbons and olefins corresponding to the olefins in the alkylation and having a second skeletal distribution different than said first skeletal distribution.

14. A process for the skeletal isomerization of linear olefins in the range of $C_4$ to $C_8$ olefins comprising:

(a) feeding an organic aromatic hydrocarbon and a $C_4$ to $C_{15}$ olefin having a first skeletal distribution into an alkylation zone containing an acidic catalyst to maintain a molar ratio of aromatic hydrocarbons:olefin in the range of 2 to 100:1 in said reaction zone under alkylation conditions to catalytically react a portion of said aromatic hydrocarbon and said olefin to form an alkylation product comprising alkylated organic aromatic hydrocarbon, unreacted aromatic hydrocarbon and unreacted olefin, (b) separating the alkylated aromatic hydrocarbon from the other components of the alkylation product, (c) feeding said alkylated organic aromatic hydrocarbon to a dealkylation zone containing acidic catalyst under dealkylation conditions to dealkylate a portion of said alkylated organic aromatic hydrocarbon to form a dealkylation product mixture comprising aromatic hydrocarbon, olefin corresponding to the olefin in the alkylation and having a second skeletal distribution different than said first skeletal distribution and alkylated organic aromatic hydrocarbon.

15. The process according to claim 14 wherein said alkylation zone comprises a distillation column reactor containing a fixed bed acidic catalytic distillation structure in a distillation reaction zone wherein concurrently:

(i) said aromatic hydrocarbon and said olefin catalytically react to form said alkylation product and (ii) said alkylation product is fractionally distilled to separate the components thereof, and said alkylated organic aromatic compound is withdrawn from said distillation column reactor.

16. The process according to claim 14 wherein said dealkylation zone comprises a distillation column reactor containing a fixed bed acidic catalytic distillation structure in a distillation reaction zone wherein concurrently:

(i) said alkylated organic aromatic hydrocarbon is catalytically dissociated into said dealkylation product and (ii) said olefin is separated from the dealkylation product and withdrawn from said distillation column reactor.

17. The process according to claim 14 wherein:
said alkylation zone comprises a distillation column reactor containing a fixed bed acidic catalytic distillation structure in a distillation reaction zone wherein concurrently:

(i) said aromatic hydrocarbon and said olefin catalytically react to form said alkylation product and (ii) said alkylation product is fractionally distilled to separate the components thereof, and said alkylated organic aromatic hydrocarbon is withdrawn from said distillation column reactor and
said dealkylation zone comprises a distillation column reactor containing a fixed bed acidic catalytic distillation structure in a distillation reaction zone wherein concurrently:

(i) said alkylated organic aromatic compound is catalytically dissociated into said dealkylation product and (ii) said olefin is separated from the dealkylation product and withdrawn from said distillation column reactor.

18. The process according to claim 14 wherein said alkylation reaction zone comprises a fixed bed straight pass reactor.

19. The process according to claim 14 wherein said dealkylation reaction zone comprises a fixed bed straight pass reactor.

20. The process according to claim 14 wherein said alkylation reaction zone comprises a fixed bed straight pass reactor and said dealkylation reaction zone comprises a fixed bed straight pass reactor.

21. The process according to claim 15 wherein said dealkylation reaction zone comprises a fixed bed straight pass reactor.

22. The process according to claim 16 wherein said alkylation reaction zone comprises a fixed bed straight pass reactor.

23. The process according to claim 14 wherein said dealkylation is carried out under conditions to selectively dealkylate branched olefins.

24. The process according to claim 23 wherein said branched olefins are separated from said dealkylation product.

25. The process according to claim 14 wherein said olefin in said dealkylation product comprises a mixture of branched olefins and linear olefins.

26. The process according to claim 25 wherein said mixture of branched olefins and linear olefins is separated from said dealkylation product.

27. The process according to claim 26 wherein said mixture of branched olefins and linear olefins are contacted with a $C_1$ to $C_8$ alcohol in the presence of an acidic catalyst under etherification conditions to selectively react a portion of the branched olefins.

28. The process according to claim 27 wherein said olefin comprises $C_4$ olefin and the branched olefins comprises tert-butylene.

29. The process according to claim 27 wherein said olefin comprises $C_5$ olefin and the branched olefins comprises isoamylene.

30. The process according to claim 14 wherein said organic aromatic hydrocarbon comprises benzene.

31. The process according to claim 14 wherein said organic aromatic hydrocarbon comprises toluene.

32. The process according to claim 14 wherein said organic aromatic hydrocarbon comprises xylenes.

\* \* \* \* \*